US006429338B1

United States Patent
Burdeniuc et al.

(10) Patent No.: US 6,429,338 B1
(45) Date of Patent: Aug. 6, 2002

(54) HYDROGENATION OF SINGLE RING AROMATIC DIAMINES

(75) Inventors: Juan Jesus Burdeniuc, Macungie; Gamini Ananda Vedage, Bethlehem; Bradley Heath Cook, Blandon, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/051,934

(22) Filed: Jan. 17, 2002

(51) Int. Cl.⁷ ............................................. C07C 209/00
(52) U.S. Cl. ........................................ 564/451; 564/450
(58) Field of Search ................................. 564/450, 451

(56) References Cited

U.S. PATENT DOCUMENTS

| | | | |
|---|---|---|---|
| 2,511,028 A | 6/1950 | Whitman | 260/563 |
| 2,606,924 A | 8/1952 | Whitman | 260/563 |
| 2,606,925 A | 8/1952 | Whitman | 260/563 |
| 2,606,928 A | 8/1952 | Barkdoll et al. | 260/563 |
| 3,450,759 A | 6/1969 | Cross et al. | 260/563 |
| 3,636,108 A | 1/1972 | Brake | 260/563 D |
| 3,644,522 A | 2/1972 | Brake et al. | 260/563 D |
| 4,754,070 A | 6/1988 | Casey et al. | 564/451 |
| 4,946,998 A | 8/1990 | Casey et al. | 564/451 |
| 5,973,207 A | 10/1999 | Vedage | 564/451 |

Primary Examiner—Samuel Barts
(74) Attorney, Agent, or Firm—Mary E. Bongiorno

(57) ABSTRACT

This invention relates to an improved process for the preparation of cyclohexylamines wherein an aromatic amine is contacted with hydrogen in the presence of a hydrogenation catalyst. The improvement resides in utilizing a hydrogenation catalyst comprised of rhodium metal, utilizing a dialkyl ether solvent, and effecting delay addition of the aromatic diamine to the reaction medium.

13 Claims, No Drawings

HYDROGENATION OF SINGLE RING AROMATIC DIAMINES

BACKGROUND OF THE INVENTION

Processes for the hydrogenation of aromatic amines have long been known. Typically, hydrogenation processes involve contacting an aromatic amine with hydrogen in the presence of a transition metal catalyst. In the hydrogenation of single ring aromatic amines such as toluenediamine, rhodium, ruthenium, nickel and cobalt are the widely used catalysts.

A problem associated with processes involving the hydrogenation of aromatic amines is one of catalyst life. Not only are aromatic amines inherently difficult to hydrogenate, various impurities often are present in the aromatic amine feedstock which act as catalyst poisons. Toluenediamine, for example, is difficult to hydrogenate and the present of ortho-toluenediamine isomers exacerbates the problem. Rapid deactivation of the catalyst, e.g., rhodium is a consequence. To effect hydrogenation of aromatic amines, and single ring aromatic diamines in particular, purification of the feed material prior to hydrogenation often is required.

Representative patents that describe the hydrogenation of aromatic amines are as follow:

U.S. Pat. Nos., 2,511,028; 2,606,924; 2,606,925 and 2,606,928 describe a process that involve the hydrogenation of a purified methylene dianiline at pressures in excess of 200 psig, preferably in excess of 1,000 psig, at temperatures within the range of 800 to 275 ° C. utilizing a ruthenium catalyst. The hydrogenation is carried out in the presence of an inert organic solvent. Examples of ruthenium catalyst used in the hydrogenation process include ruthenium oxides, such as ruthenium sesquioxides and ruthenium dioxide; and ruthenium salts.

U.S Pat. Nos. 3,696,108 and 3,644,522 describe processes for the manufacture of PACM by hydrogenation methylenedianiline. The authors found that if the ruthenium was carried upon a support and the support was alkali-moderated, the catalyst was much more active and catalytically effective in producing the desired hydrogenated PACM product. Alkali moderation was effected by contacting the catalyst and support with alkali metal hydroxide of alkali oxide; also, such alkali moderation of the catalyst could be effected prior to hydrogenation or in situ during the hydrogenation.

U.S. Pat. No. 3,450,759 discloses a process for the hydrogenation of toluenediamine and the patentees note the difficulty of the reaction and the resulting low yields. They attributed low yields in the hydrogenation process to the presence of ortho-toluenediamines. Their improved process relied on removing ortho-toluenediamines from the feed prior to hydrogenation.

U.S. Pat. Nos. 4,754,070 and 4,946,998 relate to an improved process for the hydrogenation of methylene dianiline contaminated with oligomers and formaldehyde condensates to produce bis(para-aminocyclohexyl)methane (PACM). The inhibiting characteristics of the contaminates were overcome by contacting the crude methylenedianiline and hydrogen in the presence of a two component metal catalyst comprised of rhodium and ruthenium. Alkali moderation of the catalyst was also shown to be effective.

U.S. Pat. No. 5,973,207 relates to an improved process for the hydrogenation meta-toluenediamine by carrying out the hydrogenation in the presence of rhodium and a $C_3$–$C_{10}$ secondary alcohol as a solvent. Hydrogenation of meta-toluenediamine can be carried out on samples containing about 0.3% of o-toluenediamine isomers.

BRIEF SUMMARY OF THE INVENTION

This invention relates to an improved process for the catalytic hydrogenation of aromatic amines, and particularly, a process for the catalytic hydrogenation of single ring aromatic diamines and specifically ortho-aromatic diamines. The basic process involves contacting the aromatic amine with hydrogen in the presence of a metal catalyst under conditions of hydrogenation in a reaction vessel. The improvement in the basic process resides in the steps comprising:

effecting the hydrogenation of the aromatic amine in the presence of a catalyst comprised of rhodium metal;

utilizing a $C_{4-12}$ dialkyl ether as a solvent; and, effecting delay addition of the aromatic diamine to the reaction medium. The level of unreacted aromatic amine in the reaction medium is, therefore, limited.

Significant advantages can be achieved by practicing the process and these include:

an ability to hydrogenate single ring aromatic diamines particularly ortho-aromatic diamines;

an ability to hydrogenate aromatic amines, e.g., ortho-aromatic diamines and particularly ortho-toluenediamines and achieve high selectivity; and, an ability to hydrogenate such aromatic amines and achieve excellent reaction rates and catalyst life.

DETAILED DESCRIPTION OF THE INVENTION

This invention relates to an improved process for the preparation of aromatic mines and preferably single ring aromatic diamines, such as toluenediamines, wherein the aromatic diamine is contacted with hydrogen in the presence of a rhodium hydrogenation catalyst. Specifically, the process is effective for the hydrogenation of ortho-toluenediamines to produce 1,2-diaminomethylcyclohexanes and the hydrogenation of meta-toluenediamines without effecting removal of contaminating impurities.

The aromatic amines include bridged and single ring versions. Bridged aromatic amines include methylenedianiline. The single ring aromatic amines which may be hydrogenated by this catalytic process include meta-toluenediamines, e.g., 2,4- and 2,6-meta-toluenediamines, ortho-toluenediamines, e.g., 2,3- and 3,4-ortho-toluenediamine, and ortho-, meta- and para-phenylene diamines. Typical products made by the process are 1,2-diamino-3-methyl-cyclohexane, 1,2-diamino-4-methyl-cyclohexane. Products that can be made by this process are: 1,2-diaminocyclohexane, 1,3-diaminocyclohexane, 1,4-diaminocyclohexane, 1,3-diamino-4-methyl-cyclohexane, 1,3-diamino-2-methyl-cyclohexane, 1,3-diamino-5-methyl-cyclohexane.

To effect hydrogenation of the aromatic amines, the hydrogenation catalyst is comprised of rhodium carried on a support. Other catalytic metals used in the hydrogenation process can be used in small amounts, e.g., up to about 10% by weight. Representative catalytic metals include ruthenium, palladium, nickel and cobalt. Representative supports include silica, alumina, e.g., kappa, delta, gamma and the like, titania, kielsulguhr and so forth. Typically, the rhodium is carried on the support in an amount of from 1 to 25 weight parts per 100 weight parts of support and preferably from 3 to 6 weight parts per 100 weight parts support.

To maintain high activity of the catalyst system in the hydrogenation process, it is preferred that the rhodium catalyst is alkali moderated. Alkali moderation typically involves the treatment of the catalyst and support material with an alkali metal hydroxide or alkali metal alkoxide, preferably lithium hydroxide or lithium ethoxide. Other alkali metals may be used, e.g., sodium and potassium but are not preferred. The alkali metal is added to provide from about 0.1 to 15% by weight of the rhodium metal including support. Often, moderation is done prior to reduction of the catalytic metal or following deposition of the rhodium on the support. Adding the alkali metal hydroxide to the reaction medium during the hydrogenation process may effect in situ alkali moderation.

Key to the hydrogenation process is the carrying out the hydrogenation in the presence of a $C_4$–$C_{12}$ dialkyl ether solvent. These solvents allow for liquid phase conditions to be maintained. Representative dialkyl ethers solvents suitable for practicing the invention include MTBE (methyl-teft-butyl ether), DEE (diethyl ether), THF (tetrahydrofuran), dioxanes, dioxolanes and so forth. Optionally, a small amount of other solvents can be used, e.g., from about 2 to 20 percent by weight of the total solvent used. Other solvents include aliphatic and alicyclic hydrocarbons. Examples include pentane, hexane, cyclohexane, methyl-cyclohexane, octane, cyclooctane and so forth.

The solvent is utilized in the hydrogenation process in an amount generally from about 10 to 80 weight percent of the amine introduced into the reaction vessel. Typically, the solvent is used at levels from about 50 to about 200 percent by weight of the aromatic amine, e.g., ortho-toluenediamine feed material.

Another key to the process is the use of semi-batch conditions. Under these conditions, the feed rate of the aromatic amine to the reactor vessel or the reaction medium contained in the reactor vessel is selected to match the rate of hydrogenation. In that way the contact time between the unreacted aromatic amine (ortho-diaminetolune) and the catalyst is minimized. The aromatic amine, e.g., ortho-toluenediamine is added to the reactor vessel at a rate of from about 0.02 to about 1.0 ml/min of OTD per gram of active catalyst including support, and preferably from about 0.06 to about 0.4 ml/min OTD per gram of active catalyst. The level of unreacted aromatic amine in the reaction medium should not exceed 1.5% by weight, and preferably should be within a range of from 0.1 to 0.8% by weight.

Temperatures for effecting hydrogenation range from about 130 to 220° C. with preferred temperatures of from about 140 to 195° C. Hydrogen partial pressures necessary for effecting hydrogenation of the aromatic amine feedstock range from about 500 to 4,000 psig, although modest pressures from 800 to 2,500 psig can be utilized.

The following examples are provided to illustrate various and preferred embodiments of the invention and are not intended to restrict the scope thereof.

COMPRATIVE EXAMPLE 1

Batch Hydrogenation of OTD

Prior Art Hydrogenation Procedure

To provide a control reaction for the process, a 1 liter stainless steel reactor was loaded with 12.6 g of catalyst (4% Rh/Alumina) and 480.7 g of molten and freshly distilled 2,3- and 3,4-diaminotoluene present in a ratio of 40/60 respectively (herein OTD). (OTD was selected as the candidate aromatic amine because of its difficulty to hydrogenate.) The reactor was then closed, leak checked and pressurized with nitrogen. OTD was melted at 65° C. and the mechanical stirrer was turned on and set to 240 rpm. Addition of lithium hydroxide (1.5 g of a 10 wt % aqueous solution) and sec-butanol (53 g) was carried out through the reactor feed line. The reactor was then purged and pressurized with compressed hydrogen. Hydrogenation was carried out at 180° C. and 850–900 psig hydrogen with 660 rpm mechanical agitation. After hydrogenation was effected, the reactor was cooled down to 100–110° C. and the internal pressure reduced to 110 psig to collect the liquid product.

The following table summarizes the data regarding the loading of the reactor.

TABLE 1

| Run # | OTD (g) | Secondary-Butanol (g) | 10% LiOH Solution (g) | Crude Product (g) | Reaction Time (hrs) |
|---|---|---|---|---|---|
| 1 | 480 | 53 | 1.5 | 549 | 5.03 |
| 2 | 471 | 54 | 0.0 | 535 | 2.86 |
| 3 | 478 | 53 | 0.0 | 541 | 3.33 |
| 4 | 472 | 53 | 0.0 | 539 | 3.63 |
| 5 | 444 | 49 | 0.0 | 508 | 3.75 |
| 6 | 463 | 51 | 0.0 | ND | 4.3 |
| 7 | 457 | 51 | 0.0 | ND | 5.41 |
| 8 | 465 | 52 | 1.5 | 532 | 7.58 |
| 9 | 478 | 53 | 0.0 | 537 | 7.98 |
| 10 | 489 | 55 | 0.0 | 597 | 10.21 |

The product obtained in every run was analyzed by GC which showed the of the desired product 1,2-diaminomethylcyclohexanes as well as amino-methyl cyclohexanes ("Deams", resulting from the deamination of the product) and higher molecular weight by-products resulting from the condensation of two or more cyclohexyl rings. The summary of the analytical data is shown below.

| Run # | % 1,2-DMCH | % OTD | % Deams | % Heavies |
|---|---|---|---|---|
| 1 | 73.5 | 0.0 | 1.1 | 19.9 |
| 2 | 89.7 | 1.3 | 2.0 | 7.0 |
| 3 | 89.8 | 0.1 | 1.7 | 8.3 |
| 4 | 86.0 | 0.0 | 1.8 | 9.7 |
| 5 | 83.2 | 1.6 | 1.8 | 10.9 |
| 6 | 75.0 | 4.6 | 1.4 | 17.5 |
| 7 | 73.2 | 2.9 | 2.5 | 17.6 |
| 8 | 84.9 | 8.5 | 1.3 | 3.2 |
| 9 | 82.7 | 10.6 | 1.3 | 5.0 |
| 10 | 78.7 | 12.8 | 1.3 | 4.7 |

The addition of lithium hydroxide during the first run reduced the amount of high molecular weight by-products and in the subsequent runs it improved the selectivity for 1,2-DMCH. However, the selectivity for 1,2-DMCH decreased with the number of hydrogenation cycles causing a progressive decrease in the selectivity. During the sixth and seventh use, a high percentage of high molecular weight by-products were obtained (>17%) requiring another addition of lithium hydroxide. Although the addition of lithium hydroxide in run # 8 improved the selectivity of the catalyst, substantial catalyst deactivation had occurred as evidenced by the sudden increase in the reaction times.

Because of the high level of heavy by-products obtained in most runs, it was concluded the process was unacceptable.

COMPARATIVE EXAMPLE 2

Semi-batch Hydrogenation of 80% OTD 20% Sec-butanol at High Feeding Rates in the Presence of a Heel of Sec-butanol and During the First Run The procedure of Example 1 was followed except that a 1 liter stainless steel reactor was loaded with 5.40 g of catalyst (4% Rh/Alumina), 300 ml of sec-butanol and 1.15 g of a 10% solution of lithium hydroxide. The reactor was heated to 180° C., pressurized with 850 psig of hydrogen and mechanically agitated at 800 rpm. A mixture of 80% OTD and 20% sec-butanol was introduced in the reactor using an ISCO pump equipped with a heating jacked connected to a hot water bath at a predetermined rate. The level of unreacted OTD was measured during the hydrogenation process. After hydrogenation, the reactor was cooled down to 100–110° C. and the internal pressure reduced to 110 psig to collect the liquid product. Part of the product of a run remained inside the reactor as heel for the subsequent run. The following table summarizes the data obtained for six runs.

| Run # | Added OTD (g) | Reaction Time (min) | OTD (g)/ RT (min) | Feed Rate (ml/min) | % 1,2-DAMCH | % Lights | % Heavies | % By-Products | % OTD unreacted |
|---|---|---|---|---|---|---|---|---|---|
| 1 | 390 | 322 | 1.21 | 1.04–2.08 | 89.4 | 4.7 | 0.0 | 4.7 | 0.9 |
| 2 | 280 | 240 | 1.16 | 2.08 | 86.8 | 3.3 | 3.7 | 5.0 | 1.2 |
| 3 | 345 | 270 | 1.27 | 2.08 | 77.8 | 3.5 | 4.9 | 11.0 | 2.7 |
| 4 | 400 | 400 | 1.00 | 2.08 | 76.6 | 1.1 | 5.0 | 12.0 | 5.3 |
| 5 | 390 | 500 | 0.78 | 2.08 | 77.6 | 0.6 | 4.5 | 8.0 | 9.3 |
| 6 | 400 | >680 | <0.58 | 2.08 | 70.1 | 0.5 | 7.1 | 9.7 | 12.7 |

When the reactor is fed with the an 80% OTD/20% sec-butanol mixture at high feed rates (i.e. 2.08 ml of mixture/minute or 0.38 ml/min./g catalyst), a detriment in both catalyst activity and selectivity is observed. With catalyst deactivation, final OTD (unreacted) increased to 2.7% in run3 and 12.7% by run 6.)

In going from run # 1 to run # 6, the selectivity for 1,2-DAMCH decreased from 89.4 to 70.1 with an increased production of heavy by-products from 0.0 to 7.1%, probably resulting from the condensation of two or more cyclohexyl rings. In addition, the grams of OTD hydrogenated per minute (OTD/RT) decreased from 1.21 (run # 1) to less than 0.58 (run # 6). Some catalytic deamination was evidenced by the addition of sec-butanol to 1,2-diaminomethylcyclohexane as shown by mass spectroscopy analysis (by-products with M+=185).

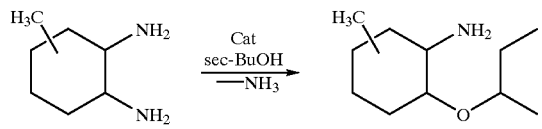

Thus, a semi-batch process using feed rates as high as 2.08 ml/min seems to provide no advantage to the performance of the catalyst in terms of activity and selectivity when compared to a batch process.

EXAMPLE 3

Semi-batch Hydrogenation of 80% OTD 20% Sec-butanol at Variable Feeding Rates in the Presence of a Heel of Sec-butanol The procedure of Example 2 was repeated except variable feed rates were used, More specifically, a 1 liter stainless steel reactor was loaded with 6.0 of catalyst (4% Rh/Alumina), 300 ml of sec-butanol and 1.5 g of a 10% solution of lithium hydroxide. The reactor was heated to 180° C., pressurized with 850 psig of hydrogen and mechanically agitated at 800 rpm. A mixture of 80% OTD and 20% sec-butanol was introduced in the reactor using an ISCO pump equipped with a heating jacked connected to a hot waterbath. The reactor was cooled down to 100–110° C. and the internal pressure reduced to 110 psig to collect the liquid product. A new heel of sec-butanol (300 ml) was introduced in the reactor after removing the product from a previous run.

The following table summarizes the data obtained for six runs.

| Run # | Added OTD (g) | Reaction Time (min) | OTD (g) RT (min) | Feed Rate (ml/min) | % 1,2-DAMCH | % Lights | % Heavies | % By-Products | % OTD unreacted |
|---|---|---|---|---|---|---|---|---|---|
| 1 | 400 | 323 | 1.23 | 2.08 | 75.6 | 0.9 | 3.9 | 19.2 | 0.0 |
| 2 | 400 | 280 | 1.42 | 2.08 | 52.9 | 0.8 | 6.1 | 40.2 | 0.0 |
| 3 | 370 | 484 | 0.76 | 2.08 | 63.3 | 1.4 | 4.2 | 30.4 | 0.6 |
| 4 | 236 | 370 | 0.63 | 0.94 | 48.3 | 1.6 | 4.3 | 45.0 | 0.8 |
| 5 | 250 | 355 | 0.70 | 0.94 | 47.9 | 2.9 | 5.7 | 42.7 | 0.8 |

Feeding the reactor at 2.08 ml/min (0.34 ml/min./g catalyst) with a mixture 80% OTD 20% sec-butanol caused a rapid decrease in catalyst activity. Thus, in going from run # 1 to run # 3, the amount of OTD hydrogenated per minute (OTD/RT) decreased from 1.23 (run # 1) to 0.76 (run # 3). Even though the presence of a new heel of sec-butanol in every run produced a high level of deamination by-products, the addition minimized the formation of heavy by-products resulting form the condensation of two or more cyclohexyl rings. Furthermore, no appreciable catalyst deactivation occurred when comparing runs # 4 and # 5 where the feeding rate was decreased from 2.08 to 0.94.

From the high level of by-products, it was believed the hydrogenation process was unacceptable.

EXAMPLE 4

Semi-batch Hydrogenation of 80% OTD 20% Sec-butanol at Variable Feed Rates in the Presence of a Heel of Sec-butanol or THF A 1 liter stainless steel reactor was loaded with 6.0 g of catalyst (4% Rh/Alumina), 300 ml of sec-butanol and 1.8 g of a 10% solution of lithium hydroxide. The reactor was heated to 180° C., pressurized with 850 psig of hydrogen and mechanically agitated at 800 rpm. A mixture of 80% OTD and 20% sec-butanol was introduced in the reactor using an ISCO pump equipped with a heating jacked connected to a hot water bath. The reactor was cooled down to 100–110° C. and the internal pressure reduced to 110 psig to collect the liquid product. A heel of 250 ml of sec-butanol (runs# 1–4), THF (run # 5) or reaction product (run # 6) was introduced in the reactor after collection of the product and prior to the next reaction.

The following table summarizes the data obtained for six runs.

| Run | Heel | Added OTD (g) | Reaction Time (min) | OTD (g)/ RT (min) | Feed Rate (ml/min) | % 1,2-DAMCH | % Lights | % Heavies | % By-Products | % OTD unreacted |
|---|---|---|---|---|---|---|---|---|---|---|
| 1 | s-BuOH | 242 | 330 | 0.73 | 0.94 | 64.0 | 2.2 | 4.5 | 28.7 | 0.5 |
| 2 | s-BuOH | 257 | 330 | 0.78 | 0.94 | 60.7 | 2.3 | 5.3 | 31.2 | 0.5 |
| 3 | s-BuOH | 254 | 335 | 0.76 | 0.94 | 61.3 | 1.8 | 3.6 | 31.7 | 0.6 |
| 4 | s-BuOH | 240 | 330 | 0.72 | 0.94 | 60.5 | 1.9 | 6.3 | 30.9 | 0.5 |
| 5 | THF | 241 | 380 | 0.63 | 0.75 | 94.7 | 0.9 | 3.3 | 0.0 | 1.2 |
| 6 | Product | 242 | 410 | 0.60 | 0.70 | 92.5 | 1.3 | 5.1 | 0.0 | 1.2 |

No appreciable catalyst deactivation occurred between runs 1–4 where a feed rate of 0.94 ml/min (0.15 ml/min//g. catalyst) was used. As in the previous examples, the apparent presence of sec-butanol caused the formation of deamination by-products. Nevertheless, the presence of the solvent seemed to minimize the production of heavies. When switching from a heel of sec-butanol to a heel of THF, a jump in the selectivity for 1,2-DAMCH occurred. It was believed this was because this non-protic solvent cannot deaminate the product. It is worth nothing that in runs # 5 and 6 a high selectivity for the desired product was accomplished. However, it is evident that in run # 6 where the heel used was the product from run # 5, a high percentage of heavies was produced.

These experiments show that minimization of heavy by-products can be accomplished using a heel of a solvent that does not induce deamination of the product, e.g., THF. Also, using a low feed rate (<2.08 ml/min) can improve the catalyst performance and thereby decrease its deactivation rate. The low feed rate data suggest that the presence of unreacted aromatic amine in the reaction medium is a factor that causes catalyst deactivation.

EXAMPLE 5

Semi-batch Hydrogenation of Neat OTD with Variable Feeding Rates and Variable Solvents A 1 liter stainless steel reactor was loaded with 6.0 g of catalyst (4% Rh/Alumina), 300 ml of sec-butanol and 2.1 g of a 10% solution of lithium hydroxide. The reactor was heated to 180° C., pressurized with 850 psig of hydrogen and mechanically agitated at 800 rpm. Molten OTD was introduced in the reactor using an ISCO pump equipped with a heating jacked connected to a hot water bath. The reactor was cooled down to 100–110° C. and the internal pressure reduced to 110 psig to collect the liquid product. A heel of 250 ml of THF was used only for the first run. After the first run, the product from a run was used as heel for the next run with the exception of run # 6 that used 250 ml of MTBE as heel.

The following table summarizes the data obtained for six runs.

| Run | Heel | Added OTD (g) | 10 % LiOH (g) | Reaction Time (min) | OTD (g)/ RT (min) | Feed Rate (ml/min) | % 1,2-DAMCH | % Lights | % Heavies | % OTD unreacted |
|---|---|---|---|---|---|---|---|---|---|---|
| 1 | THF | 246 | 2.1 | 390 | 0.63 | 0.70 | 92.0 | 1.9 | 5.5 | 0.8 |
| 2 | Product | 250 | 0.0 | 470 | 0.53 | 0.70 | 89.5 | 2.0 | 7.3 | 1.3 |
| 3 | Product | 240 | 0.0 | 470 | 0.51 | 0.65 | 88.2 | 2.1 | 8.7 | 1.0 |
| 4 | Product | 228 | 0.0 | 530 | 0.43 | 0.50 | 79.0 | 2.3 | 17.8 | 1.0 |
| 5 | Product | 210 | 0.0 | 540 | 0.39 | 0.40 | 71.0 | 2.8 | 25.4 | 0.7 |
| 6 | MTBE | 260 | 1.6 | 750 | 0.35 | 0.40 | 87.8 | 3.4 | 8.5 | 0.4 |

Runs 2–5 show the decreasing selectivity obtained when the product from a run (mostly 1,2-DAMCH) is used as heel for the next run. An increase from 5.5 to 25.4% in the amount of heavies is observed in going from run # 1 to # 5.

To compensate for decreasing catalyst activity, the rate of addition of OTD was progressively decreased to minimize the time the contact of unreacted OTD with the catalyst and prevent its poisoning. Because the selectivity for 1,2-DMACH dropped from 92.0% (run # 1) to 71% (run # 5) activation treatment of the catalyst with lithium hydroxide was believed necessary. Although the treatment partially restored the selectivity (run # 6, the % selectivity=87.8%), the catalyst activity following the treatment decreased as evidenced by the longer reaction time required in runs # 5 and # 6. (The OTD feed rate was used 0.4 ml/min.)

Run 6 shows that catalyst life can be improved by addition of the dialkyl ether solvent MTBE. Selectivity increase to 87.8% with a substantial decrease in heavy by-products. Although, some of the increase may have been attributable to the addition of LiOH, other data suggest that LiOH was not the sole contributing factor.

EXAMPLE 6

Semi-batch Hydrogenation of OTD with Constant Feed Rates in the Presence of MTBE as Heel for Every Run The procedure of Example 2 was repeated except that a 1 liter stainless steel reactor was loaded with 5.9 g of catalyst (4% Rh/Alumina), 250 ml of methyl tertiary butyl ether (MTBE) and 1.4 g of a 10% solution of lithium hydroxide. The reactor was heated to 180° C., pressurized with 850 psig of hydrogen and mechanically agitated at 800 rpm. Molten OTD was introduced in the reactor using an ISCO pump equipped with a heating jacked connected to a hot water bath. The reactor was cooled down to 100–110° C. and the internal pressure reduced to 110 psig to collect the liquid product.

The following table summarizes the data obtained for six runs.

These runs show the advantage of using MTBE as the solvent for the hydrogenation in combination with a delay addition of OTD to achieve high selectivity of 1,2-DAMCH. This is clearly reflected in the much smaller and almost constant % of heavies obtained for these runs. Adding OTD at a feed rate comparable to the hydrogenation rate helped minimize the contact time of unreacted OTD with the catalyst and thereby reducing by-product. Improved catalyst life and activity is evidenced by the almost constant ratio of reacted OTD per unit of time (OTD/RT).

In terms of solvent type, using a heel of MTBE in every run caused a dramatic improvement in the selectivity for 1,2-DAMCH without incurring the formation of by-products as in the case of sec-butanol. Yields (>97%) and selectivities (>97%) were obtained.

Although not intending to be bound by theory, the approach employing delay addition and the use of MTBE helped maintain a low % of heavies in the product and because of the lower level of heavies, further activation treatment with lithium hydroxide in later runs was not necessary. Thus, it was possible to avoid the complication of catalyst deactivation resulting from the differing treatment as shown in EXAMPLE 5.

In summary, Examples 1–5 describe the limitations encountered when attempting to hydrogenate ortho-toluenediamines using conventional methods. In a batch process (Example 1) catalyst deactivation is observed probably because of the extensive contact between the catalyst and the ortho-diaminotoluene. Examples 2-4 show that a hindered alcohol such as sec-butanol (and alcohols in general) can result in a relatively high % of by-products thereby decreasing the overall yield and selectivity for 1,2-diaminomethylcyclohexane. Examples 3–6 show that a heel of solvent in every run is desirable for maintaining the catalyst activity. If a dialkyl ether solvent heel is present only in the first run (Example 2) and the product from a run is used as heel for the next run, then catalyst poisoning occurs resulting in slower rates and poor selectivities.

What is claimed is:

1. In a process for the heterogeneous catalytic hydrogenation of an aromatic amine in a reactor vessel which comprises contacting the single ring aromatic amine with

| Run | Heel | Added OTD (g) | 10 % LiOH (g) | Reaction Time (min) | OTD (g)/ RT (min) | Feed Rate (ml/min) | % 1,2-DAMCH | % Lights | % Heavies | % OTD unreacted |
|---|---|---|---|---|---|---|---|---|---|---|
| 1 | MTBE | 244 | 1.4 | 480 | 0.50 | 0.70 | 84.8 | 2.8 | 6.0 | 6.3 |
| 2 | MTBE | 247 | 0.0 | 470 | 0.52 | 0.70 | 94.1 | 2.2 | 3.5 | 0.2 |
| 3 | MTBE | 234 | 0.0 | 470 | 0.50 | 0.70 | 96.1 | 1.7 | 1.8 | 0.3 |
| 4 | MTBE | 238 | 0.0 | 440 | 0.54 | 0.70 | 98.5 | 1.4 | 0.0 | 0.2 |
| 5 | MTBE | 242 | 0.0 | 450 | 0.53 | 0.70 | 97.2 | 1.5 | 1.2 | 0.1 |
| 6 | MTBE | 245 | 0.0 | 460 | 0.53 | 0.70 | 96.4 | 1.5 | 1.7 | 0.3 | hydrogen in the presence of a metal catalyst under conditions of hydrogenation while in the reactor vessel, the improvement which resides in the steps comprising:

effecting the hydrogenation of the aromatic amine in the presence of a catalyst comprised of rhodium metal;

utilizing a $C_{4-12}$ dialkyl ether as a solvent; and, effecting delay addition of the aromatic amine to the reactor vessel.

2. The process of claim 1 wherein the aromatic amine is a single ring aromatic diamine.

3. The process of claim 2 wherein the dialkyl ether is selected from the group consisting of methyl-tert-butyl ether, diethyl ether, tetrahydrofuran, dioxane, and dioxolane.

4. The process of claim 3 wherein a dialkyl ether heel is in contact with the rhodium catalyst prior to contact with the single ring aromatic diamine.

5. The process of claim 4 wherein the delay rate of addition of the single ring aromatic diamine to the reactor vessel is from 0.02 to about 1.0 ml/min of aromatic diamine per gram of catalyst including support.

6. The process of claim 5 wherein the level of unreacted aromatic diamine in the reactor vessel does not exceed 1.5% by weight.

7. The process of claim 6 wherein the aromatic diamine is toluenediamine.

8. The process of claim 7 wherein the toluenediamine is an ortho-toluenediamine.

9. The process of claim 8 wherein the ortho-toluenediamine is delayed to the reactor vessel in an amount of from about 0.06 to about 0.4 ml/min ortho-toluenediamine per gram of catalyst.

10. The process of claim 9 wherein the dialkyl ether solvent is methyl-tert-butyl ether.

11. The process of claim 10 wherein the level of unreacted ortho-toluenediamine in the reactor vessel is maintained at a level of less than 1% by weight.

12. The process of claim 11 wherein the pressure in the reactor vessel ranges from 800 to 2500 psig.

13. The process of claim 12 wherein the catalyst is activated with lithium hydroxide.

* * * * *